United States Patent
Pochorovski et al.

(10) Patent No.: US 10,703,853 B1
(45) Date of Patent: Jul. 7, 2020

(54) SQUARATE COMPOSITIONS

(71) Applicants: Covestro Deutschland AG, Leverkusen (DE); COVESTRO LLC, Pittsburgh, PA (US)

(72) Inventors: Igor Pochorovski, Bergisch Gladbach (DE); Alan Ekin, Coraopolis, PA (US)

(73) Assignees: COVESTRO DEUTSCHLAND AG, Leverkusen (DE); COVESTRO LLC, Pittsburgh, PA (US)

( * ) Notice: Subject to any disclaimer, the term of this patent is extended or adjusted under 35 U.S.C. 154(b) by 36 days.

(21) Appl. No.: 16/269,595

(22) Filed: Feb. 7, 2019

(51) Int. Cl.
| | | |
|---|---|---|
| *C08G 18/83* | (2006.01) | |
| *C08J 3/24* | (2006.01) | |
| *C09D 175/04* | (2006.01) | |
| *C09K 3/10* | (2006.01) | |
| *C07D 265/34* | (2006.01) | |
| *C09J 175/04* | (2006.01) | |

(52) U.S. Cl.
CPC ......... *C08G 18/833* (2013.01); *C07D 265/34* (2013.01); *C08J 3/24* (2013.01); *C09D 175/04* (2013.01); *C09J 175/04* (2013.01); *C09K 3/1021* (2013.01); *C07C 2601/04* (2017.05); *C07C 2602/00* (2017.05); *C09K 2200/065* (2013.01)

(58) Field of Classification Search
CPC .............. C07D 265/34; C07C 2601/04; C07C 2602/00; C07C 2602/02; C08G 18/833; C08J 3/24; C09D 175/04; C09J 175/04; C09K 3/1021; C09K 2200/065
See application file for complete search history.

(56) References Cited

U.S. PATENT DOCUMENTS

2011/0111012 A1* 5/2011 Pepper .............. A61F 13/00995
424/445

* cited by examiner

*Primary Examiner* — Christopher M Rodd
(74) *Attorney, Agent, or Firm* — John E. Mrozinski, Jr.

(57) ABSTRACT

A cross-linker composition, a resin composition, a curable composition, a method of making thereof, and articles produced therefrom are provided. The cross-linker composition can be formed from by contacting a diethanolamine with a dialkylsquarate to form the cross-linker composition. The resin composition can be formed by contacting the cross-linker composition with an isocyanate. The curable composition can be formed by contacting the resin composition with an amine.

24 Claims, No Drawings

SQUARATE COMPOSITIONS

FIELD OF THE INVENTION

The present invention relates to a cross-linker composition, a resin composition, a curable composition, a method of making thereof, and articles produced therefrom.

BACKGROUND OF THE INVENTION

Two-component polyurethane forming compositions are widely used because of the many advantageous properties they exhibit. These compositions generally comprise a liquid binder component and a liquid hardener/crosslinker component. The liquid binder component may comprise an isocyanate-reactive component, such as a polyol, and the liquid crosslinker component may comprise a polyisocyanate. The addition reaction of the polyisocyanate with the isocyanate-reactive component, which can occur at ambient conditions, can produce crosslinked polyurethane networks that form coatings.

SUMMARY OF THE INVENTION

It is understood that the invention disclosed and described in this specification is not limited to the embodiments summarized in this Summary. The reader will appreciate the foregoing details, as well as others, upon considering the following detailed description of various non-limiting and non-exhaustive embodiments according to this specification.

In one aspect, a cross-linker composition is provided. The cross-linker composition comprises the following structure:

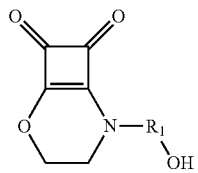

wherein $R_1$ is an alkyl bridging group.

In another aspect, a method of forming a cross-linker composition is provided. The method comprises reacting a diethanolamine with a dialkylsquarate to form the cross-linker composition, the cross-linker composition comprising the formula:

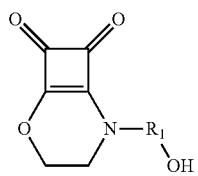

wherein $R_1$ is an alkyl bridging group.

In yet another aspect, a method of forming a resin composition is provided. The method comprises reacting a cross-linker composition with an isocyanate to form the resin composition, the cross-linker composition comprising the formula:

wherein $R_1$ is an alkyl bridging group.

DETAILED DESCRIPTION OF THE INVENTION

Various embodiments are described and illustrated herein to provide an overall understanding of the structure, function, operation, manufacture, and use of the disclosed products and processes. The various embodiments described and illustrated herein are non-limiting and non-exhaustive. Thus, the invention is not limited by the description of the various non-limiting and non-exhaustive embodiments disclosed herein. Rather, the invention is defined solely by the claims. The features and characteristics illustrated and/or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be present in the prior art. The various embodiments disclosed and described in this specification can comprise, consist of, or consist essentially of the features and characteristics as variously described herein.

Any patent, publication, or other disclosure material identified herein is incorporated herein by reference in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference herein.

Reference herein to "certain examples," "some examples," "various non-limiting examples," or the like, means that a particular feature or characteristic may be included in an example. Thus, use of such phrases, and similar phrases, herein does not necessarily refer to a common example, and may refer to different examples. Further, the particular features or characteristics may be combined in any suitable manner in one or more examples. Thus, the particular features or characteristics illustrated or described in connection with various examples may be combined, in whole or in part, with the features or characteristics of one or more other examples. Such modifications and variations are intended to be included within the scope of the present specification. In this manner, the various examples described in this specification are non-limiting and non-exhaustive.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

The grammatical articles "a", "an", and "the", as used herein, are intended to include "at least one" or "one or more", unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

As used herein, "polymer" encompasses prepolymers, oligomers and both homopolymers and copolymers; the prefix "poly" in this context referring to two or more.

As used herein, the term "aliphatic" refers to organic compounds characterized by substituted or un-substituted straight, branched, and/or cyclic chain arrangements of constituent carbon atoms. Aliphatic compounds do not contain aromatic rings as part of the molecular structure thereof.

As used herein, the term "cycloaliphatic" refers to organic compounds characterized by arrangement of carbon atoms in closed ring structures. Cycloaliphatic compounds do not contain aromatic rings as part of the molecular structure thereof. Therefore, cycloaliphatic compounds are a subset of aliphatic compounds. Therefore, the term "aliphatic" encompasses aliphatic compounds and/or cycloaliphatic compounds.

As used herein, "isocyanate" refers to a compound containing an isocyanate group. The isocyanate can comprise at least one of a monoisocyanate and a polyisocyanate. As used herein, "diisocyanate" refers to a compound containing two isocyanate groups. As used herein, "polyisocyanate" refers to a compound containing two or more isocyanate groups. Hence, diisocyanates are a subset of polyisocyanates.

As used in this specification, the terms "cure" and "curing" refer to a chemical crosslinking of components in a curable composition and/or a chain extension of the curable composition. Accordingly, the terms "cure" and "curing" do not encompass solely physical drying of curable compositions through solvent or carrier evaporation. In this regard, the term "cured," as used in this specification, refers to the condition of a curable composition in which a component of the curable composition has chemically reacted to form a new covalent bond.

Having a free isocyanate group or reacting an isocyanate group to cure a curable composition may be undesirable. Thus, a cross-linker composition, a resin composition, a curable composition, a method of making thereof, and articles produced therefrom are provided which can minimize and/or can eliminate free isocyanate groups and/or a reaction of isocyanate groups during curing of a curable composition. Namely, the inventive cross-linker can comprise Formula I and/or an isomer thereof.

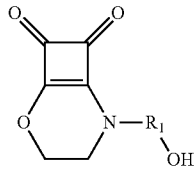

Formula I $R_1$ can be an alkyl bridging group. As used herein, an "alkyl bridging group" means a methylene bridging group (e.g., —CH2-) or a chain of single bonded carbons (e.g., —CH2-CH2-, —CH2-CH2-CH2-). R1 may not present in Formula I and the hydroxyl group can be directly attached to the amine group. In various examples, $R_1$ is a —CH2-CH2- group and the cross-linker can comprise Formula II and/or an isomer thereof.

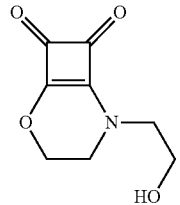

Formula II

The cross-linker composition can comprise a reaction product of diethanolamine and a dialkyl squarate. For example, the reaction of diethanolamine and a dialkyl squarate to form the cross-linker composition of Formula II is illustrated in Scheme I.

Scheme I

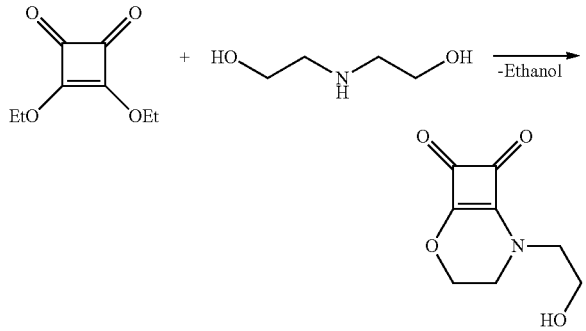

The cross-linker composition can be contacted with a first isocyanate to form a resin composition. The first isocyanate can react with the hydroxyl group in the cross-linker composition to form an adduct comprising a carbamate (e.g., urethane). The resin composition may include minimal, if any, free isocyanate groups. For example, the resin composition may not include any free isocyanate groups. The reaction of the cross-linker composition comprising Formula I and the first isocyanate to form a resin composition comprising Formula III is illustrated in Scheme II.

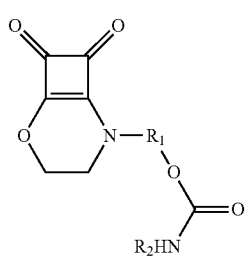

Formula III $R_2$ is an alkyl group or an aryl group.

Scheme II

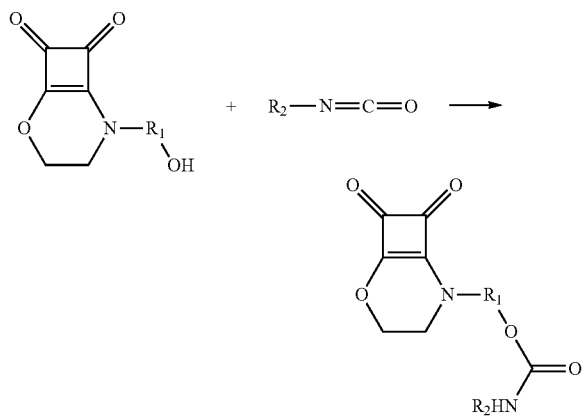

An isocyanate can comprise a mono-isocyanate or a polyisocyanate. In various examples comprising a polyisocyanate, the adduct may include two or more units of the cross-linker composition per polyisocyanate. For example, if the polyisocyanate is a diisocyanate, the adduct can comprise two units of cross-linker composition per polyisocyanate.

The polyisocyanate can comprise at least one of an aromatic polyisocyanate, an araliphatic polyisocyanate, and an aliphatic polyisocyanate. In various examples, the isocyanate can comprise at least one of a polyurethane resin, a polyurea resin, an acrylic resin, a polyester resin, a polycarbonate resin, a polysiloxane resin, an epoxy resin, a melamine resin, and a phenol formaldehyde resin. For example, the isocyanate can comprise at least one of 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyantocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydro-toluene diisocyanate, toluene diisocyanate (TDI), diphenylmethane diisocyanate (MDI), PDI (pentane diisocyanate—bio-based), and isomers thereof.

In some examples, the isocyanate can comprise a diisocyanate of the formula $R_x(NCO)_2$, wherein $R_x$ represents an aliphatic hydrocarbon residue having 4 to 12 carbon atoms, a cycloaliphatic hydrocarbon residue having 6 to 15 carbon atoms, an aromatic hydrocarbon residue having 6 to 15 carbon atoms or an araliphatic hydrocarbon residue having 7 to 15 carbon atoms. In various examples, the isocyanate has an isocyanate calculated functionality of two or more such as, for example, three or more (calculated from isocyanate content and number average molecular weight, determined by Gel Permeation Chromatography (GPC) measurement).

In various examples, the isocyanate can comprise at least one of a polyisocyanate comprising a biuret group, such as the biuret adduct of hexamethylene diisocyanate (HDI) available from Covestro AG under the trade designation DESMODUR N-100, a polyisocyanate containing an isocyanurate group, such as that available from Covestro AG under trade designation DESMODUR N-3300, a polyisocyanate such as that available from Covestro AG under the tradename DESMODUR N-3600, which has a viscosity of 800-1400 mPa·s at 25° C., and a polyisocyanate containing at least one of an iminooxadiazine dione group, a urethane group, a uretdione group, a carbodiimide group, and a allophonate group.

In various examples, in forming the resin composition according to the present disclosure, the isocyanate and cross-linker composition are combined in relative amounts such that the resin composition has a ratio of isocyanate groups to isocyanate-reactive groups (e.g., hydroxyl group) in an effective ratio for a curing process. For example, the resin composition has a ratio of isocyanate groups to isocyanate-reactive groups (e.g., hydroxyl group) of 0.01:1 to 3.0:1, such as, for example, 0.8:1 to 3.0:1, 0.5:1 to 2.0:1, 0.8:1 to 2.0:1, 0.8:1 to 1.2:1, 0.9:1 to 1:1, 0.9:1 to 1.1:1, 1:1 to 1.1:1, 1:1 to 1.8:1, or 1:1 to 1.5:1. In certain examples, the resin composition has a ratio of isocyanate groups to isocyanate-reactive groups (e.g., hydroxyl group) of at least 0.01:1, such as, for example, at least 0.5:1, at least 0.8:1, at least 0.9:1, at least 1:1, at least 1.1:1, at least 1.2:1, at least 1.5:1, or at least 2.0:1. In certain examples, the resin composition has a ratio of isocyanate groups to isocyanate-reactive groups (e.g., hydroxyl group) of no greater than 3.0:1, such as, for example, no greater than 2.0:1, no greater than 1.5:1, no greater than 1.2:1, no greater than 1.1:1, no greater than 1.1:1, no greater than 0.9:1, no greater than 0.8:1, or no greater than 0.5:1.

In various examples, the resin composition can comprise a catalyst for the reaction between the isocyanate-reactive group and the isocyanate group. The catalyst can comprise at least one of a metallic catalyst and a nonmetallic catalyst, such as, for example, an amine catalyst (e.g., 1,8-diazabicyclo[5.4.0]undec-7-ene (DBU), 1,4-diazabicyclo[2.2.2]octane (DABCO) or triethanolamine), a Lewis acid compound (e.g., dibutyltin dilaurate), lead octoate, tin octoate, a titanium complex, a zirconium complex, a cadmium compound, a bismuth compound (e.g., bismuth neodecanoate), and an iron compound. In various examples, the catalyst can be present in the resin composition in an amount of no more than 1.0% by weight based on the total solids contents of the composition.

In various examples where the cross-linker comprises formula II, the cross-linker can react with the first isocyanate to form a resin composition comprising formula III as shown in scheme III.

Formula IV

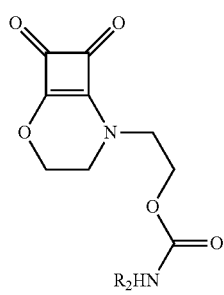

R₂ is an alkyl group or an aryl group.

Scheme III

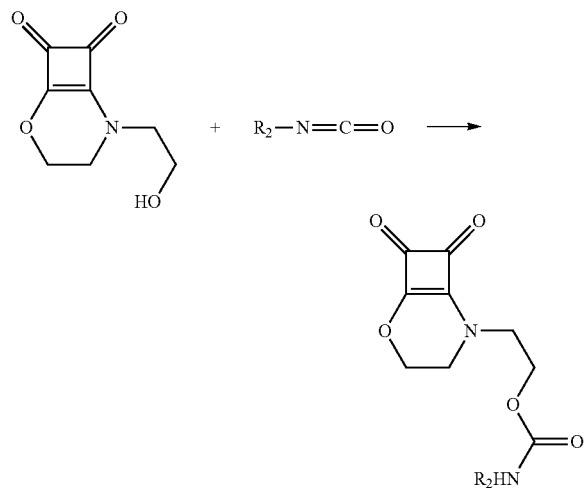

The resin composition can be reacted with an amine to form the curable composition. The curable composition can be an adduct of the amine and the resin composition. In various examples, the reaction of the resin composition with the amine may not include the reaction of a free isocyanate group. The reaction of the resin composition and the amine can comprise a ring opening reaction. For example, the amine can react with the ester group present in the resin composition to dissolve the bond between the oxygens in the ester group and, thus, open the ring of the cycloaliphatic compound in the resin composition. In various examples, the reaction of the resin composition and the amine can comprise a cross-linking of the resin composition with the amine (e.g., 0.01-100% crosslinked). For example, the reaction of the resin composition comprising formula III and the amine to form the curable composition comprising formula V is illustrated in Scheme IV.

Formula V

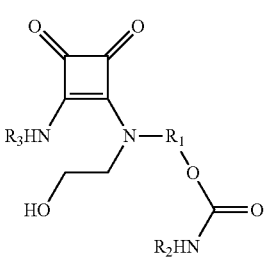

R₃ is an alkyl group or an aryl group.

Scheme IV

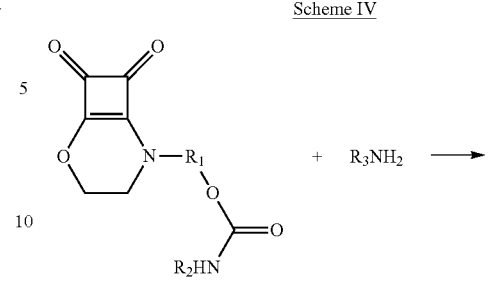

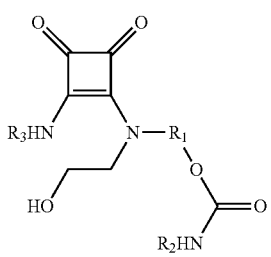

In various examples, the amine is a primary amine. In various examples, the amine comprises at least one of diethylenetriamine, 2-methylpentamethylenediamine, isophrone diamine, 4,4'-diaminodicyclohexylmethane, 3,3'-dimethyl-4,4'diaminodicyclohexylmethane, polyether amine, and a polyaspartic ester based amine.

In various examples where the resin composition comprises formula IV, the resin composition can react with an amine to form the curable composition comprising formula VI as illustrated in Scheme V.

Formula VI

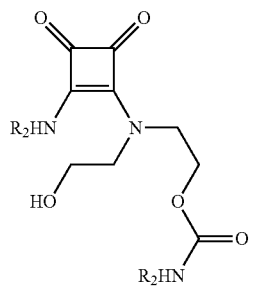

R₃ is an alkyl group or an aryl group.

Scheme V

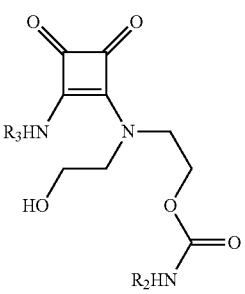

In various examples, the curable composition can be reacted with an additional reactant (X) to form a secondary composition. The additional reactant can react with the free hydroxyl group in the curable composition comprising Formula V to form the secondary composition comprising Formula VII as illustrated in Scheme VI.

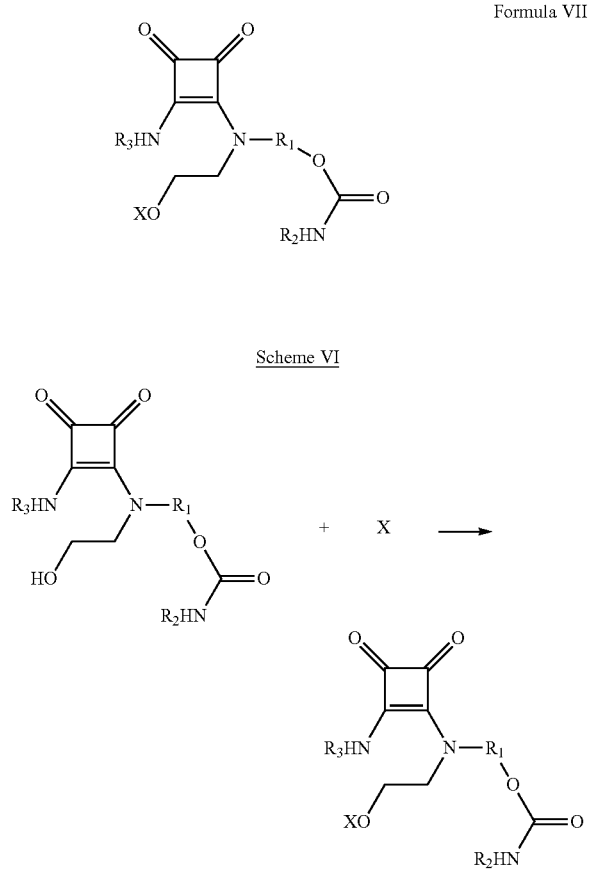

Scheme VI

The additional reactant can be various chemicals suitable to react with the free hydroxyl group in the curable composition. In various examples, the additional reactant may be a second isocyanate, a silane, and a melamine. The second isocyanate may be different than or the same as the first isocyanate. In various examples where the first and second isocyanates differ, the curable composition can comprise unique properties otherwise unattainable with only the first isocyanate or only the second isocyanate.

In various examples where the curable composition comprises formula VI, the reaction of the curable composition with a second isocyanate to form the secondary composition comprising formula VIII is illustrated in scheme VII.

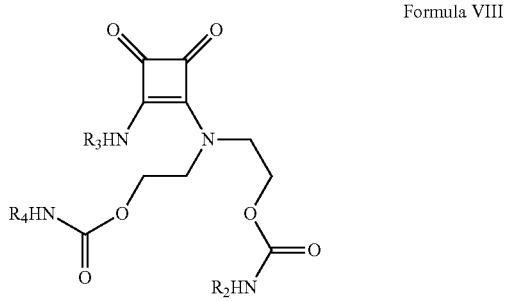

Scheme VII

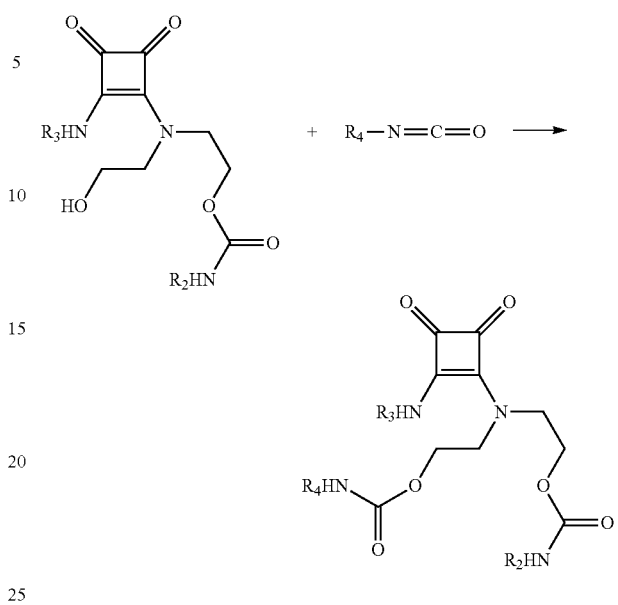

$R_4$ is an alkyl group or an aryl group. $R_2$ and $R_4$ can be the same alkyl or aryl group or can comprise a different alkyl group or aryl group. In various examples, $R_2$ and $R_4$ can comprise at least one of an aliphatic hydrocarbon residue having 4 to 12 carbon atoms, a cycloaliphatic hydrocarbon residue having 6 to 15 carbon atoms, an aromatic hydrocarbon residue having 6 to 15 carbon atoms or an araliphatic hydrocarbon residue having 7 to 15 carbon atoms. For example, $R_2$ and $R_4$ both can comprise butane. In certain examples, $R_2$ can comprise butane while $R_4$ can comprise hexane. In various examples, $R_2$ can comprise hexane while $R_4$ can comprise cyclopentane. The method according to the present disclosure can enable the addition of different chemical groups to the secondary composition through the use of at least two different reaction steps with two different isocyanates.

Schemes II-VII illustrate a subunit of a polymer through different stages of a polymerization reaction and should not be considered limiting of a length, configuration, and/or molecular weight of a polymer that can be formed. The isocyanate and amine depicted in Schemes II-VII can have various amounts of active groups as describe herein. Thus, the isocyanate and resulting structures shown in Schemes II-VII should not be limited to a monoisocyanate and can be a polyisocyanate as described herein. The amine and resulting structures shown in Schemes IV-VII should not be limited to a monoamine and can be a polyamine as described herein.

The curable composition and/or secondary composition can be cured to form an article. The curable composition and/or secondary composition can be cured at a temperature in a range of 0° C. to 200° C., such as, for example, 20° C. to 150° C., 25° C. to 140° C., or 80° C. to 140° C. In various examples, the curable composition and/or secondary composition can be cured at a temperature of at least 20° C., such as, for example, at least 25° C., at least 50° C., at least 80° C., at least 100° C., at least 140° C., or at least 150° C. The curable composition and/or secondary can be cured for at least 1 minute, such as, for example, at least 1 hour, at least 2 hours, at least 3 hours, at least 5 hours, at least 10 hours, at least 15 hours, at least 16 hours, or at least 24 hours.

The article can be, for example, a component of at least one of an adhesive, a coating, a casting, a sealant, an elastomer, and a foam.

The cured curable composition and/or cured secondary composition can have a microhardness of at least 2 N/mm², such as, for example, at least 4 N/mm², at least 8 N/mm², at least 10 N/mm², at least 20 N/mm², at least 25 N/mm², at least 50 N/mm², at least 100 N/mm², at least 125 N/mm², or at least 140 N/mm². The microhardness can be measured according to DIN EN ISO 14577-1:2015.

The cured curable composition and/or cured secondary composition can have a methyl ethyl ketone rub resistance of at least 100 double rubs, such as, for example, at least 150 double rubs, at least 180 double rubs, at least 200 double rubs, at least 250 double rubs, or at least 300 double rubs. The methyl ethyl ketone rub resistance can be measured according to ASTM D4752-10(2015).

The cured curable composition and/or cured secondary composition can have a cross-hatch adhesion of at least 4B. For example, the cured curable composition and/or cured secondary composition can have a cross-hatch adhesion of 5B. The cross hatch-adhesion can be measured according to ASTM D 3359-17.

The cured curable composition and/or cured secondary composition can have a direct and reverse impact strength of at least 100 in-lbs, such as, for example, at least 150 in-lbs. Direct and reverse impact strength can be measured according to ASTM D 2794-93(2019).

The cured curable composition and/or cured secondary composition can have a water spot resistance of at least 1 hour, such as, for example, at least 2 hours, at least 10 hours, at least 20 hours, or at least 24 hours. Water spot testing can be measured according to ASTM E 1793-17.

The cured curable composition and/or cured secondary composition can have a percent elongation of less than 10%, such as, for examples, less than 5%, less than 2%, less than 1%, or less than 0.1%. For example, the cured curable composition and/or cured secondary composition can have a percent elongation of 0. The percent elongation can be measured according to ASTM D 522/D522M-17.

The curable composition and/or secondary composition according to the present disclosure can comprise formula IX and/or an isomer thereof.

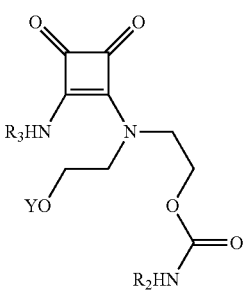

Formula IX $R_1$ can be an alkyl bridging group. $R_2$ can be an alkyl group or an aryl group. Y can be at least one of a hydrogen atom, an alkyl group, an aryl group, and a carbamate group. In various examples, Y can comprise a carbamate group and at least one of an alkyl group and an aryl group. In various examples, Y can be a hydrogen atom. In various examples, $R_2$ and Y can comprise an alkyl group or an aryl group that differ from one another. In some examples, $R_2$ and Y can comprise the same alkyl or aryl group.

Example

The non-limiting and non-exhaustive prophetic example that follows is intended to further describe various non-limiting and non-exhaustive embodiments without restricting the scope of the embodiments described in this disclosure. Although the present disclosure describes a coating in the Example, those skilled in the art will appreciate it can also be equally applicable to an adhesive, a casting, a sealant, an elastomer, and a foam.

All quantities given in "parts" and "percent" are understood to be by weight, unless otherwise indicated.

Cross-linker composition comprising Formula II can be produced. More specifically, in a 250 mL round bottom flask, 96 mL of dialkylsquarate can be added to 150 mL of isopropanol and mixed. In an addition funnel, 75.0 parts diethanolamine can be dissolved in 60 mL isopropanol and mixed. The diethanolamine mixture can be added to the dialkylsquarate mixture drop-wise at room temperature and mixed for 12 hours to form the cross-linker composition comprising Formula II. The formed cross-linker composition comprising Formula II can be filtered, washed with isopropanol, and dried in a vacuum oven.

The formed cross-linker composition can be reacted with DESMODUR N-3600 available from Covestro AG (Leverkusen, Germany) to obtain a resin composition. The synthesis can be performed at 50° C. for several hours using T-12 catalyst (e.g., dibutylin bilaurate). Dimethylformamide (DMF) and acetone can be added to reduce viscosity.

The amines A-H as shown in Table 1 can be used to prepare a curable composition.

TABLE I

| | |
|---|---|
| Amine A | Diethylenetriamine (DETA) |
| Amine B | 2-Methylpentamethylenediamine, commercially available from Invista as DYTEK A |
| Amine C | Isophorone diamine (IPDA) |
| Amine D | 4,4'-Diaminodicyclohexylmethane (PACM) |
| Amine E | 3, 3'-dimethyl-4, 4'-Diaminodicyclohexylmethane, commercially available from BASF as LAROMIN C260 |
| Amine F | Polyether amine commercially available from Huntsman as JEFFAMINE D-400 |
| Amine G | Polyaspartic ester based amine, commercially available from Covestro as DESMOPHEN NH 1420 |
| Amine H | Polyaspartic ester based amine, commercially available from Covestro as DESMOPHEN NH 1220 |

In order to create a curable composition, acetone can be added to the resin composition. The mixture can be contacted with and reacted with an amine from Table I using a FLACKTEK speed mixer for one minute followed by application to a panel using a drawdown bar. The panel can be an iron phosphate treated ACT B1000, 4"×12" (10.2 cm×30.5 cm) test panel, an aluminum chromate treated panel 4"×12" (10.2 cm×30.5 cm) test panel, or an untreated aluminum 4"×12" (10.2 cm×30.5 cm) test panel. The dry film thickness of the curable composition can be 15 μm on the panels. The curable composition can be cured on the panels at various conditions such as, room temperature (e.g., 25° C.) f or 16 hours, 80° C. for 16 hours, and 140° C. for three hours.

It is believed that the curable composition would have improved properties such as MEK double rubs, microhardness, impact strength, elongation, water resistance, and/or cross-hatch adhesion as compared to the prior art. Additionally, other curable compositions formulated according to the present disclosure additionally can have improved performance characteristics.

Various aspects of the invention according to the present disclosure include, but are not limited to, the aspects listed in the following numbered clauses.

Clause 1. A cross-linker composition comprising the formula:

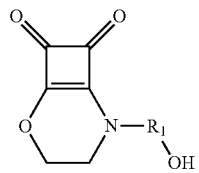

wherein $R_1$ is an alkyl group.

Clause 2. A resin composition formed from a reaction product of the cross-linker composition according to Clause 1 and an isocyanate.

Clause 3. The resin composition according to Clause 2, wherein the cross-linker composition comprises a reaction product of a diethanolamine and a dialkylsquarate.

Clause 4. The resin composition according to one of Clauses 2 and 3, wherein the resin composition has the formula:

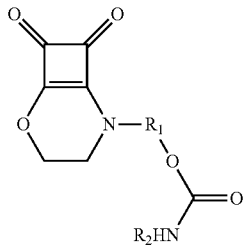

wherein $R_1$ is an alkyl group; and
wherein $R_2$ is an alkyl group or an aryl group.

Clause 5. The resin composition according to any one of Clauses 2 to 4, wherein the isocyanate has a functionality of at least 2.

Clause 6. A resin composition according to any one of Clauses 2 to 5, wherein the isocyanate is selected from the group consisting of 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyantocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydro-toluene diisocyanate, toluene diisocyanate (TDI), diphenylmethane diisocyanate (MDI), PDI (pentane diisocyanate—bio-based), isomers thereof, and combinations thereof.

Clause 7. The resin composition according to any one of Clauses 2 to 6, wherein the isocyanate comprises at least one of a polyurethane resin, a polyurea resin, an acrylic resin, a polyester resin, a polycarbonate resin, a polysiloxane resin, an epoxy resin, a melamine resin, and a phenol formaldehyde resin.

Clause 8. A curable composition comprising a reaction product of the resin composition according to any one of Clauses 2 to 7 and an amine.

Clause 9. The curable composition according to Clause 6, wherein the curable composition comprises the formula:

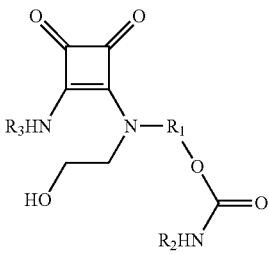

wherein $R_1$ is an alkyl group;
wherein $R_2$ is an alkyl group or an aryl group; and
wherein $R_3$ is an alkyl group or an aryl group.

Clause 10. The curable composition according to one of Clauses 8 and 9, wherein the amine comprises a primary amine.

Clause 11. The curable composition according to any one of Clauses 8 to 10, wherein the amine comprises at least one of diethylenetriamine, 2-methylpentamethylenediamine, isophrone diamine, 4,4'-diaminodicyclohexylmethane, 3,3'-dimethyl-4,4'diaminodicyclohexylmethane, polyether amine, and a polyaspartic ester based amine.

Clause 12. The curable composition according to any one of Clauses 8 to 11, wherein the curable composition has a free hydroxyl group.

Clause 13. A secondary composition comprising a reaction product of the curable composition according to any one of Clauses 8 to 12 with a second isocyanate, wherein the second isocyanate is different than the first isocyanate.

Clause 14. A secondary composition comprising a reaction product of the curable composition according to any one of Clauses 8 to 12 with a second isocyanate, wherein the second isocyanate is the same as the first isocyanate.

Clause 15. An article formed from the curable composition according to any one of Clauses 8 to 12.

Clause 16. The article according to Clause 15, wherein the article is a component of at least one of a coating, a casting, a sealant, an adhesive, an elastomer, and a foam.

Clause 17. A method of forming a cross-linker composition comprising: reacting a diethanolamine with a dialkylsquarate to form the cross-linker composition, the cross-linker composition comprising the formula:

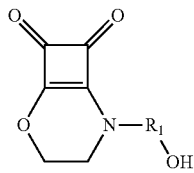

wherein $R_1$ is an alkyl group.

Clause 18. A method of forming a resin composition, comprising: reacting a cross-linker composition with an isocyanate to form the resin composition, the cross-linker composition comprising the formula:

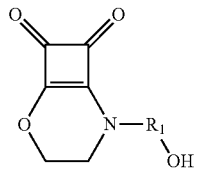

wherein R₁ is an alkyl group.

Clause 19. The method according to Clause 18, further comprising reacting the resin composition with an amine to form a curable composition.

Clause 20. The method according to one of Clauses 18 and 19, wherein reacting further comprises cross-linking the resin composition with the amine.

Clause 21. The method according to any one of Clauses 18 to 20, wherein cross-linking the resin further comprises a ring opening reaction.

Clause 22. The method according to any one of Clauses 18 to 21, further comprising contacting the curable composition with a second isocyanate to form a secondary curable composition, wherein the second isocyanate is different than or the same as the first isocyanate.

Clause 23. The method according to anyone of Clauses 18 to 22, further comprising curing the curable composition to form an article.

Clause 24. The method according to Clause 23, wherein the article is a component of at least one of an adhesive, a coating, a casting, a sealant, an elastomer, and a foam.

What is claimed is:

1. A cross-linker composition comprising the formula:

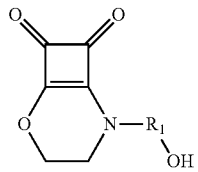

wherein R₁ is an alkyl group.

2. A resin composition formed from a reaction product of the cross-linker composition according to claim 1 and an isocyanate.

3. The resin composition according to claim 2, wherein the cross-linker composition comprises a reaction product of a diethanolamine and a dialkylsquarate.

4. The resin composition according to claim 2, wherein the resin composition has the formula:

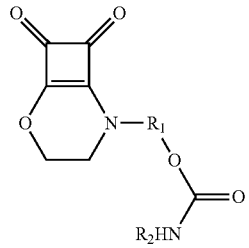

wherein R₁ is an alkyl group; and
wherein R₂ is an alkyl group or an aryl group.

5. The resin composition according to claim 2, wherein the isocyanate has a functionality of at least 2.

6. The resin composition according to claim 2, wherein the isocyanate is selected from the group consisting of 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyantocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydro-toluene diisocyanate, toluene diisocyanate (TDI), diphenylmethane diisocyanate (MDI), PDI (pentane diisocyanate—biobased), isomers thereof, and combinations thereof.

7. The resin composition according to claim 2, wherein the isocyanate comprises at least one of a polyurethane resin, a polyurea resin, an acrylic resin, a polyester resin, a polycarbonate resin, a polysiloxane resin, an epoxy resin, a melamine resin, and a phenol formaldehyde resin.

8. A curable composition comprising a reaction product of the resin composition according to claim 2 and an amine.

9. The curable composition according to claim 8, wherein the curable composition comprises the formula:

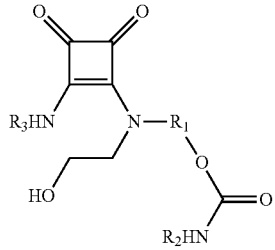

wherein R₁ is an alkyl group;
wherein R₂ is an alkyl group or an aryl group; and
wherein R₃ is an alkyl group or an aryl group.

10. The curable composition according to claim 8, wherein the amine comprises a primary amine.

11. The curable composition according to claim 8, wherein the amine comprises at least one of diethylenetriamine, 2-methylpentamethylenediamine, isophrone diamine, 4,4'-diaminodicyclohexylmethane, 3,3'-dimethyl-4,4'diaminodicyclohexylmethane, polyether amine, and a polyaspartic ester based amine.

12. The curable composition according to claim 8, wherein the curable composition has a free hydroxyl group.

13. A secondary composition comprising a reaction product of the curable composition according to claim 8 with a second isocyanate, wherein the second isocyanate is different than the first isocyanate.

14. A secondary composition comprising a reaction product of the curable composition according to claim 8 with a second isocyanate, wherein the second isocyanate is the same as the first isocyanate.

15. An article formed from the curable composition according to claim 8.

16. The article according to claim 15, wherein the article is a component of at least one of a coating, an adhesive, a casting, a sealant, an elastomer, and a foam.

17. A method of forming a cross-linker composition comprising: reacting a diethanolamine with a dialkylsquarate to form the cross-linker composition, the cross-linker composition comprising the formula:

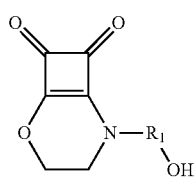

wherein R₁ is an alkyl group.

18. A method of forming a resin composition, comprising: reacting a cross-linker composition with an isocyanate to form the resin composition, the cross-linker composition comprising the formula:

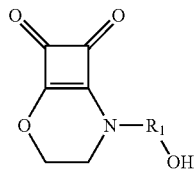

wherein R₁ is an alkyl group.

19. The method according to claim 18, further comprising reacting the resin composition with an amine to form a curable composition.

20. The method according to claim 18, wherein reacting further comprises cross-linking the resin composition with the amine.

21. The method according to claim 20, wherein cross-linking the resin further comprises a ring opening reaction.

22. The method according to claim 18, further comprising contacting the curable composition with a second isocyanate to form a secondary curable composition, wherein the second isocyanate is different than or the same as the first isocyanate.

23. The method according to claim 18, further comprising curing the curable composition to form an article.

24. The method according to claim 23, wherein the article is a component of at least one of an adhesive, a coating, a casting, a sealant, an elastomer, and a foam.

* * * * *